United States Patent
Konno et al.

(10) Patent No.: US 10,888,223 B2
(45) Date of Patent: Jan. 12, 2021

(54) VITAL SIGNS SENSOR, SIGNAL PROCESSING DEVICE, AND IDENTIFIER STORAGE DEVICE

(71) Applicant: Nihon Kohden Corporation, Tokyo (JP)

(72) Inventors: Norihito Konno, Tokyo (JP); Hirohiko Ikeya, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 216 days.

(21) Appl. No.: 15/774,499

(22) PCT Filed: Nov. 8, 2016

(86) PCT No.: PCT/JP2016/004833
§ 371 (c)(1),
(2) Date: May 8, 2018

(87) PCT Pub. No.: WO2017/081863
PCT Pub. Date: May 18, 2017

(65) Prior Publication Data
US 2019/0090741 A1   Mar. 28, 2019

(30) Foreign Application Priority Data
Nov. 9, 2015   (JP) .................... 2015-219878

(51) Int. Cl.
*A61B 5/00* (2006.01)
*G16H 40/63* (2018.01)
*A61B 5/024* (2006.01)

(52) U.S. Cl.
CPC .......... *A61B 5/0002* (2013.01); *A61B 5/6814* (2013.01); *A61B 5/6823* (2013.01);
(Continued)

(58) Field of Classification Search
CPC ... A61B 5/0002; A61B 5/6814; A61B 5/6823; A61B 5/6824; A61B 5/6826;
(Continued)

(56) References Cited

U.S. PATENT DOCUMENTS

| 6,346,886 B1* | 2/2002 | De La Huerga ...... A61J 7/0481 340/573.1 |
| 2009/0062626 A1* | 3/2009 | Baldus ................ A61B 5/0205 600/301 |

(Continued)

FOREIGN PATENT DOCUMENTS

| JP | 2003-058866 A | 2/2003 |
| JP | 2005-168624 A | 6/2005 |

(Continued)

OTHER PUBLICATIONS

International Search Report issued in Patent Application No. PCT/JP2016/004833 dated Feb. 6, 2017.
(Continued)

*Primary Examiner* — Scott M. Getzow
(74) *Attorney, Agent, or Firm* — Pearne & Gordon LLP

(57) ABSTRACT

A vital signs sensor includes an identifier storage device that stores an identifier of a subject, and a signal processing device that acquires a vital sign from the subject, and that wirelessly transmits the vital sign and the identifier that is stored in the identifier storage device, with correlating the vital sign with the identifier, wherein the identifier storage device has a structure where the identifier storage device is attachable to and detachable from the signal processing device.

12 Claims, 10 Drawing Sheets

(52) U.S. Cl.
CPC .......... *A61B 5/6824* (2013.01); *A61B 5/6826* (2013.01); *A61B 5/6828* (2013.01); *A61B 5/6832* (2013.01); *A61B 5/6833* (2013.01); *G16H 40/63* (2018.01); *A61B 5/02438* (2013.01); *A61B 5/7495* (2013.01); *A61B 2560/0214* (2013.01); *A61B 2560/045* (2013.01); *A61B 2560/0475* (2013.01); *A61B 2562/08* (2013.01); *A61B 2562/227* (2013.01)

(58) Field of Classification Search
CPC ... A61B 5/6828; A61B 5/6833; A61B 5/6832; A61B 5/02438; A61B 5/7495; A61B 2560/045; A61B 2560/0214; A61B 2562/227; A61B 2560/0475; A61B 2562/08; G16H 40/63
See application file for complete search history.

(56) References Cited

U.S. PATENT DOCUMENTS

| | | |
|---|---|---|
| 2009/0299157 A1 | 12/2009 | Telfort et al. |
| 2011/0125535 A1 | 5/2011 | Gross |
| 2013/0060098 A1 | 3/2013 | Thomsen et al. |
| 2013/0115881 A1 | 5/2013 | Liao et al. |
| 2016/0095543 A1 | 4/2016 | Telfort et al. |

FOREIGN PATENT DOCUMENTS

| | | | |
|---|---|---|---|
| JP | 2011-519684 A | | 7/2011 |
| JP | 2012-500698 A | | 1/2012 |
| JP | 2013-098980 A | | 5/2013 |
| JP | 2013-515528 A | | 5/2013 |
| WO | 2006/059156 | * | 6/2006 |
| WO | 2006-059156 A1 | | 6/2006 |
| WO | 2009-036316 A1 | | 3/2009 |
| WO | 2009-137524 A2 | | 11/2009 |

OTHER PUBLICATIONS

Written Opinion issued in Patent Application No. PCT/JP2016/004833 dated Feb. 6, 2017.

Japanese Office action issued in Japanese Patent Application No. 2015-219878 dated Oct. 9, 2019.

\* cited by examiner

VITAL SIGNS SENSOR, SIGNAL PROCESSING DEVICE, AND IDENTIFIER STORAGE DEVICE

TECHNICAL FIELD

The present invention relates to a sensor which is to be attached to the body of a subject, and which wirelessly transmits a signal corresponding to vital signs information of the subject.

BACKGROUND ART

When vital signs information of the subject is to be measured, a wireless vital signs sensor is used in order to prevent the subject from feeling inconvenience and uncomfortableness due to wiring. The wireless vital signs sensor transmits the vital sign acquired from the subject, to a receiver.

In the receiver, the condition of the subject must be managed with correlating the received vital sign with the subject. In the case where correlation between the vital sign and the subject is manually set in the receiver, the operator must carefully set the correlation because the receiver is often disposed in a place remote from the subject.

Therefore, the operation of correlating a vital sign with a subject is preferably performed in the vicinity of the subject. Patent Literature 1 discloses a method in which an identifier of a subject is previously stored in a vital signs sensor, and not only a vital sign but also the identifier are transmitted from the vital signs sensor to a receiver.

CITATION LIST

Patent Literature

[PTL 1]
JP-T-2013-515528

SUMMARY OF INVENTION

Technical Problem

Even in the case where the above-described vital signs sensor in which the identifier of a subject is stored is used, when the subject is to be changed, the identifier must be cautiously changed. When, after measurement on a certain subject is ended, the vital signs sensor is to be used in the next subject, the stored identifier must be changed to the identifier of the next subject. If the change of the identifier is forgotten, the acquired vital sign is correlated with the previous subject. In order to prevent such a situation from occurring, the operator must cautiously perform correlation.

The invention has been conducted in order to mainly solve such a problem. It is an object of the invention to provide a vital signs sensor, signal processing device, and identifier storage device in which an identifier of a subject can be adequately changed.

Solution to Problem

According an aspect of the invention, a vital signs sensor may include an identifier storage device which stores an identifier of a subject and a signal processing device which acquires a vital sign from the subject, and which wirelessly transmits the vital sign and the identifier that is stored in the identifier storage device, with correlating the vital sign with the identifier. The identifier storage device may have a structure where the identifier storage device is attachable to and detachable from the signal processing device.

Advantageous Effects of Invention

According to the vital signs sensor, the identifier can be adequately changed.

DESCRIPTION OF EMBODIMENTS

Figure 1:
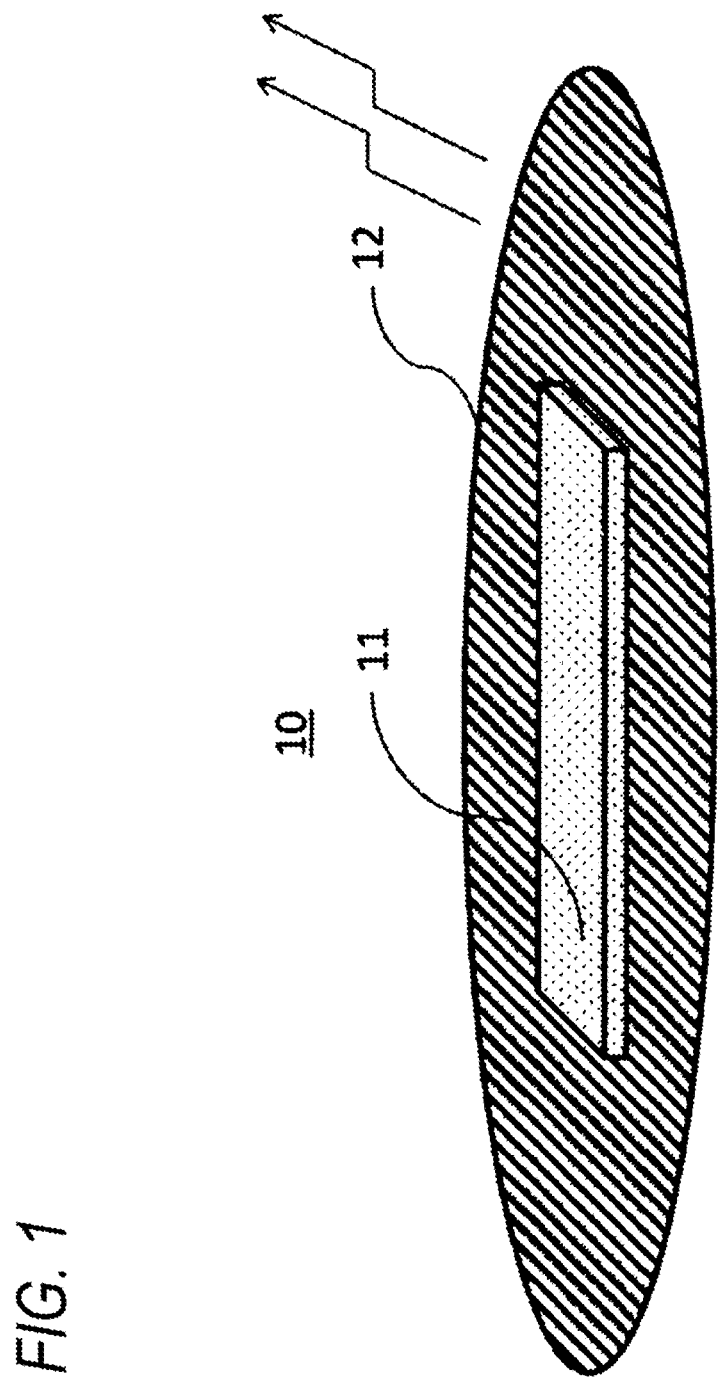
FIG. 1 is a configuration diagram of the vital signs sensor of the invention.

Embodiments of the invention will be described with reference to the drawings. In the drawings used in the following description, in order to make the components to have a recognizable size, their scales are appropriately changed.

FIG. 1 illustrates that a vital signs sensor 10 has a configuration including a signal processing device 11 and an identifier storage device 12. Although, in FIG. 1, the identifier storage device 12 is illustrated to be larger than the signal processing device 11, the signal processing device 11 may be configured to be larger than the identifier storage device 12.

Figure 2:
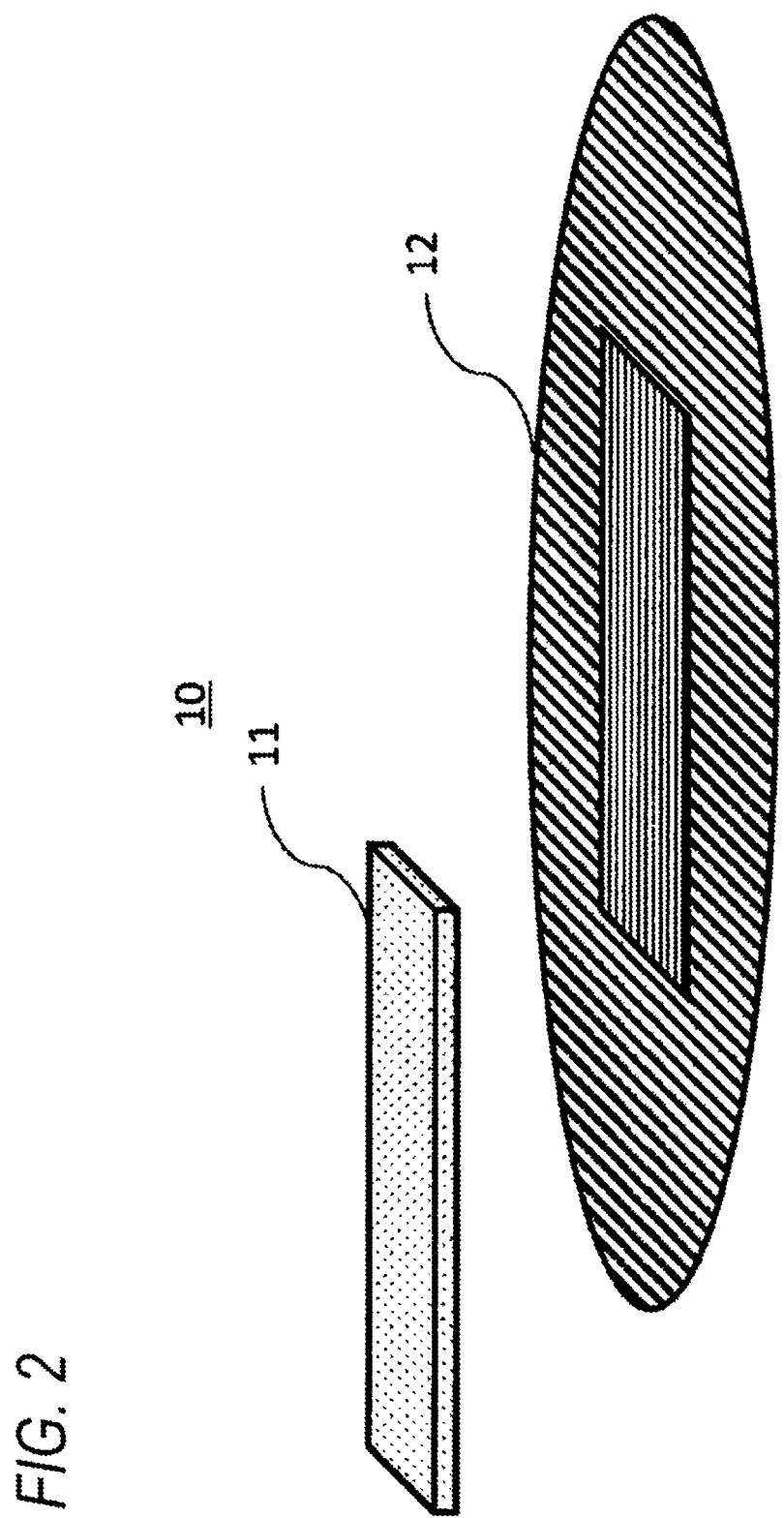
FIG. 2 is a configuration diagram of the vital signs sensor of the invention.

FIG. 2 illustrates a state where the signal processing device 11 and identifier storage device 12 which constitute the vital signs sensor 10 are separated from each other. The vital signs sensor 10 has a structure where the identifier storage device 12 can be attached to and detached from the signal processing device 11.

Figure 3:
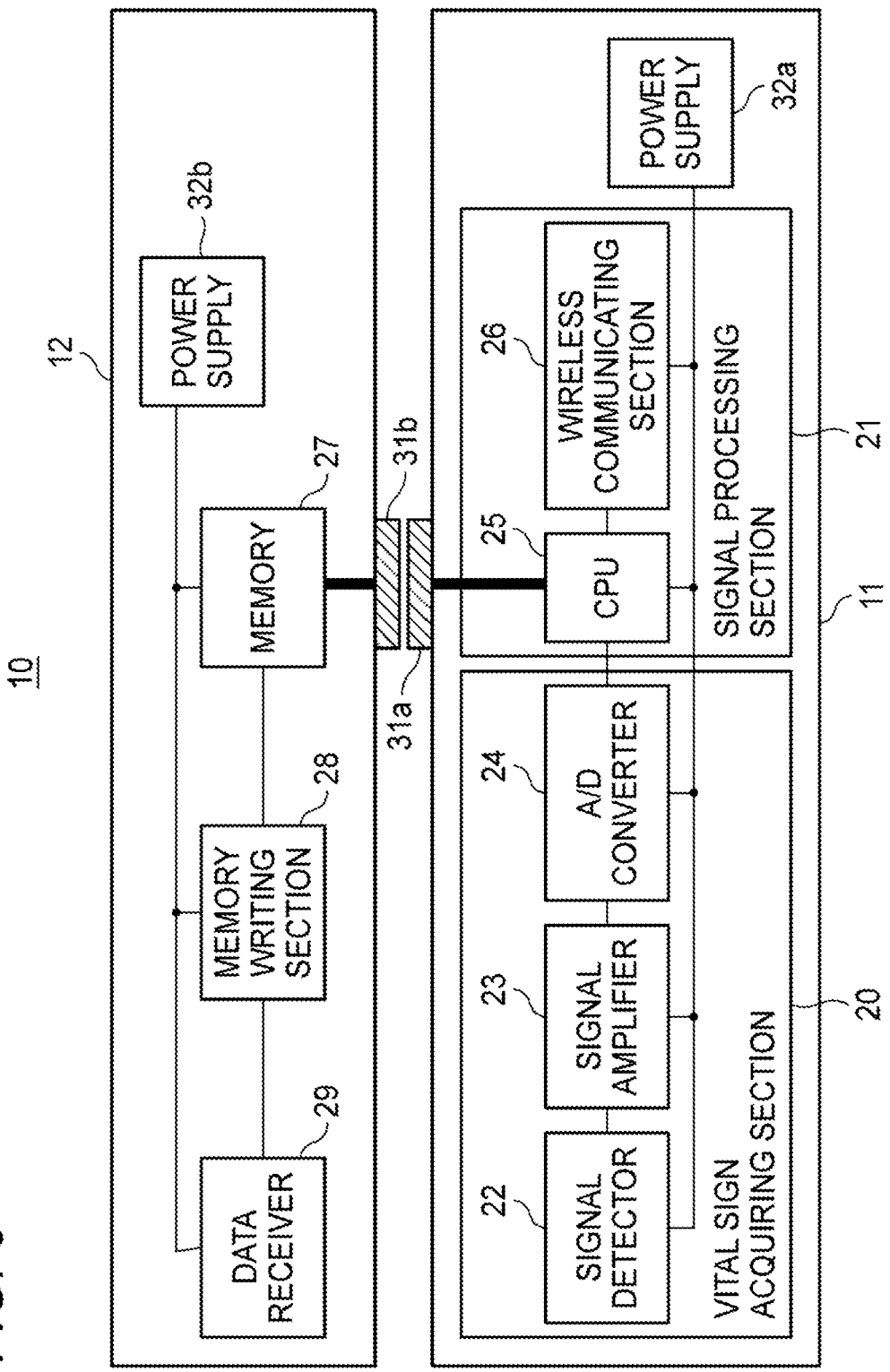
FIG. 3 is a functional configuration diagram of the vital signs sensor of the invention.

FIG. 3 diagrammatically illustrates the functional configuration of the vital signs sensor 10 of an embodiment. In FIG. 3, electrical wirings connecting between the signal processing device 11 and the identifier storage device 12 are indicated by thick lines (this will be applicable also to the other figures). The vital signs sensor 10 is attached to the body of a subject 80. The vital signs sensor 10 acquires vital signs information of the subject 80, and wirelessly transmits the acquired vital signs information and a stored identifier.

Sometimes, a single receiver which receives wireless transmission may manage vital signs information of a plurality of subjects. Even a receiver which manages one subject at one time sometimes changes the subject to be managed. Examples of such a receiver may be an installation-type apparatus which centrally manages a plurality of subjects, and a portable-type apparatus which performs remote management. The receiver manages a plurality of subjects, and changes the subject to be managed. Therefore, the receiver must correctly know the subject from whom the received vital signs information is acquired. If an identifier is included together with vital signs information in the information which is wirelessly transmitted, the receiver can easily know that the vital signs information is acquired from the subject.

The identifier is a code which is used in the receiver which receives the wireless transmission, for recognizing the individuality of the subject 80. Therefore, the identifier is configured by information from which the receiver can recognize the subject 80. The information is set as information which is held by the receiver. The identifier may have various modes depending on a receiver so long as the receiver can recognize the subject oneself with the identifier.

The signal processing device 11 may include a vital sign acquiring section 20 and a signal processing section 21. The signal processing device 11 acquires vital signs information of the subject 80, reads out the identifier of the subject 80 which is stored in the identifier storage device 12, and wirelessly transmits the vital signs information and the identifier.

The vital sign acquiring section 20 detects a vital sign, and outputs the vital sign to the signal processing section 21. Examples of the vital sign are the biopotential, the body temperature, the pulse rate, the arterial oxygen saturation, the blood glucose level, and the number of walking steps. The biopotential may be a value indicating a change of the potential of vital signs information. Examples of the biopotential are the electrocardiogram, the impedance respiration, the thermistor respiration, the heart rate, the cardiac output, the brain wave, and the electromyogram.

The vital sign acquiring section 20 may include a signal detector 22, a signal amplifier 23, an A/D converter 24, and the like. The signal detector 22 detects a vital sign, and outputs the vital sign to the signal amplifier 23. The signal amplifier 23 amplifies the input vital sign, and outputs the amplified signal to the A/D converter 24. The A/D converter 24 converts the amplified signal to a digital signal, and outputs the digital signal to the signal processing section 21. The signal detector 22, the signal amplifier 23, and the A/D converter 24 may have various modes in accordance with the acquired vital sign.

The signal processing section 21 may include a central processing unit (CPU) 25, a wireless communicating section 26, and the like. The CPU 25 receives the vital sign (digital signal) from the vital sign acquiring section 20. The CPU 25 converts the digital signal into a format according to a predetermined wireless communication method, and then outputs the converted digital signal to the wireless communicating section 26. Moreover, the CPU 25 reads out the identifier of the subject 80 from the identifier storage device 12, converts the read-out identifier into a format according to the predetermined wireless communication method, and then outputs the converted identifier to the wireless communicating section 26.

The wireless communicating section 26 wirelessly transmits the vital sign and identifier which are processed in the CPU 25, to the receiver by using the predetermined wireless communication method. Examples of the predetermined wireless communication method are BLE (Bluetooth Low Energy, Bluetooth is a registered trademark), ZigBee (registered trademark), ANT+ (registered trademark), NFC (Near Field Communication), and WiFi (registered trademark).

The signal processing device 11 may include a power supply 32a. The power supply 32a supplies electric power to the vital sign acquiring section 20, the signal processing section 21, etc.

The signal processing device 11 may include an attaching/detaching portion 31a, and the identifier storage device 12 may include an attaching/detaching portion 31b. The attaching/detaching portions 31a, 31b indicate a joining place through which the identifier storage device 12 is to be attached to and detached from the signal processing device 11. For example, the attaching/detaching portions 31a, 31b may have a structure where both the attaching/detaching portions 31a, 31b have connector shape. In this structure, the attaching/detaching portions 31a, 31b may be configured so as to be directly connector-connected, or to be connected to each other by a cable.

The identifier storage device 12 may include a memory 27. The memory 27 is configured so as to store the identifier of the subject 80, and allow the signal processing device 11 to read out the identifier.

According to the embodiment which has been described above, the attachment/detachment of the identifier storage device 12 enables the vital signs sensor 10 to handle the identifier of the subject 80 as an article. In other words, the identifier storage device 12 itself can be deemed as an identifier having a substantial shape. Originally, an identifier is configured by electronic information, and therefore cannot be visually recognized. Consequently, it is difficult to manage an identifier. If an identifier can be handled as an article, the identifier can be set or changed in an easy-to-understand manner.

Figure 4:
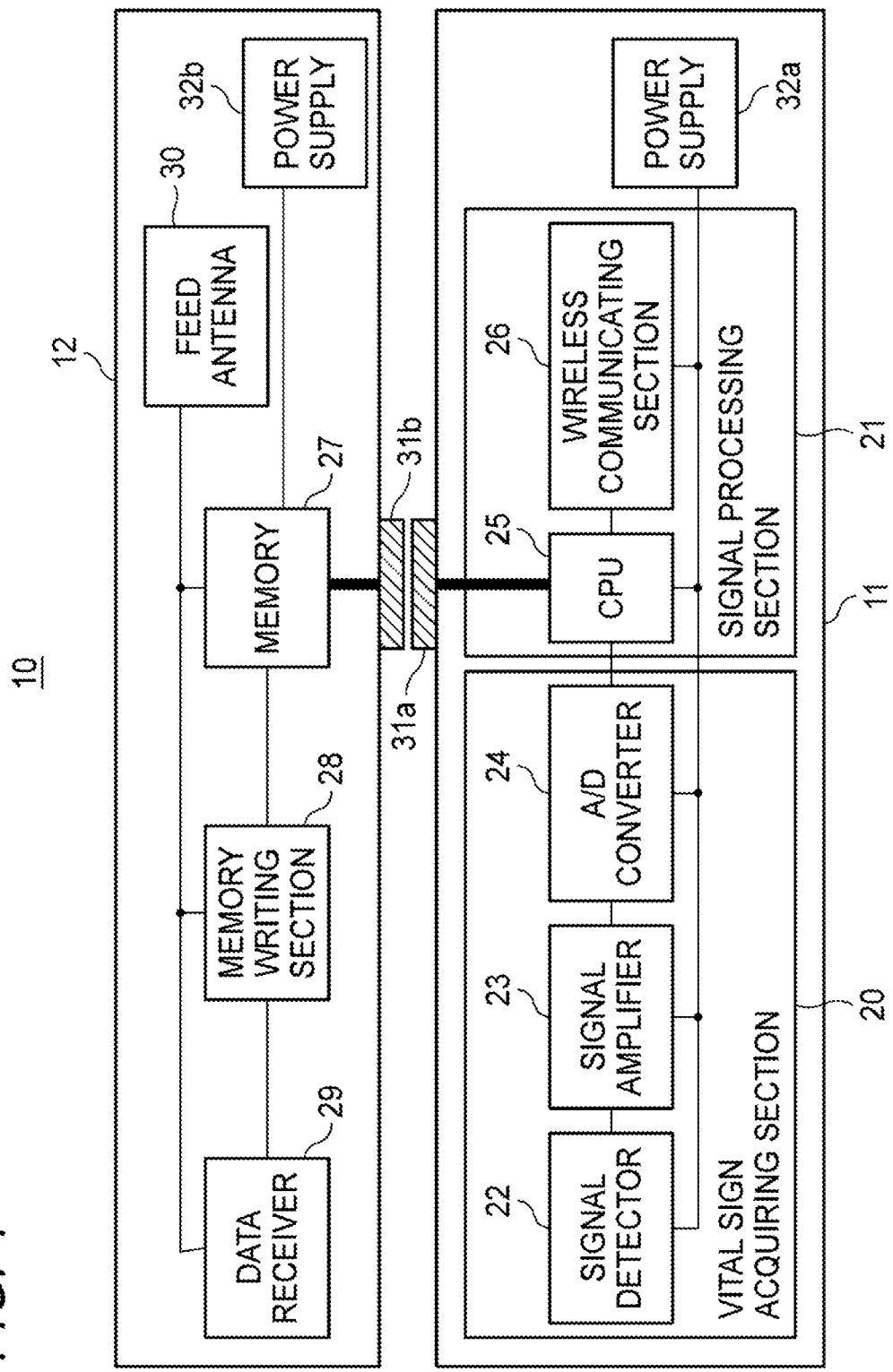
FIG. 4 is a functional configuration diagram of the vital signs sensor of the invention.

The identifier storage device 12 may include a memory writing section 28 and a data receiver 29. The data receiver 29 receives the identifier of the subject 80 from the outside, and outputs the received identifier to the memory writing section 28. An example of the communication method of the data receiver 29 is NFC. When this example is employed, an identifier can be easily written by using an NFC writer. As illustrated in FIG. 4, the identifier storage device 12 may further include a feed antenna 30, and power may be supplied from the NFC writer to the identifier storage device 12.

The identifier storage device 12 may further include a power supply 32b. The power supply 32b supplies electric power to the memory 27, the memory writing section 28, the data receiver 29, etc. In the case where the feed antenna 30 is disposed, the power supply from the power supply 32b to the memory writing section 28 and the data receiver 29 is not necessary as illustrated in FIG. 4. This is because the memory writing section 28 and the data receiver 29 are required to operate only when the identifier of the subject 80 is to be received from the outside.

The memory writing section 28 is electrically connected to the data receiver 29 and the memory 27, and writes the identifier received from the data receiver 29, in the memory 27. In the case where an identifier is already written in the memory 27, the memory writing section 28 rewrites the memory 27 by using the identifier which is newly received. In this example, an identifier can be easily written or rewritten from the outside.

The vital signs sensor 10 may be configured so as to, in the case where an identifier stored in the memory 27 does not have a predetermined format, wirelessly transmit an identifier invalidity status to the memory 27 instead of an identifier. Examples of such a case where an identifier does not have a predetermined format are a case where nothing is written in the memory 27, and that where the size of written data is extremely large or small. According to the configuration, even in the case such as that where it has been forgotten to write the identifier, that where a situation occurs which is so emergent that there is no time to write an identifier, or that where wrong data other than an identifier are written in the memory 27, the vital signs sensor 10 can wirelessly transmit a vital sign. The identifier invalidity status is configured by a code which is preset to be invalid in the receiver. According to the configuration, the receiver which receives the identifier invalidity status can manage vital signs information while suspending the operation of correlating vital signs information and the subject 80, and.

Figure 5:
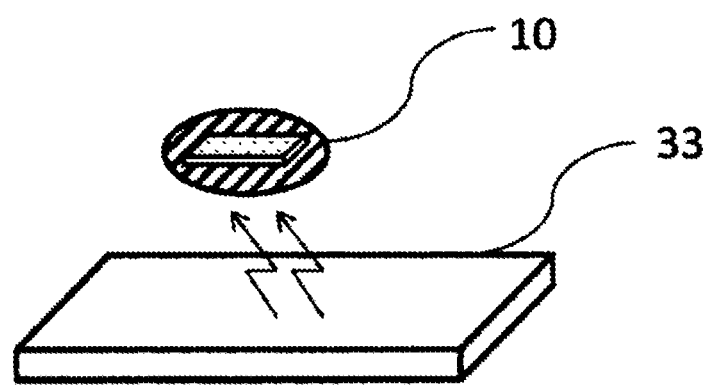
FIG. 5 is a diagram illustrating writing in which an identifier is written an external device in the vital signs sensor of the invention.

FIG. 5 illustrates a manner in which an external device 33 writes an identifier in the vital signs sensor 10. A configuration which is necessary for writing an identifier is disposed in the identifier storage device 12, and, even in a state where the signal processing device 11 is detached, an identifier can be written. However, it is preferable to enable an identifier to be written only in a state where the signal processing device 11 is attached to the identifier storage device 12. When such a limitation is set, writing of an identifier is performed immediately before the vital signs sensor 10 is used, and therefore more correct writing of an identifier is ensured.

Hereinafter, configuration modes in which writing of an identifier is enabled only in a state where the signal processing device 11 is attached to the identifier storage device 12 will be described. A first mode is programmed to firstly set a writing limitation by default on the memory 27. The signal processing device 11 may include a detecting mechanism for detecting a connection to the identifier storage device 12, and, when the signal processing device 11 detects the connection, cancels the writing limitation on the memory 27 of the identifier storage device 12. In other words, the signal processing device 11 allows writing of an identifier in the identifier storage device 12. According to the configuration, in the state where the signal processing device 11 is attached to the identifier storage device 12, the writing limitation on the memory 27 is canceled, and therefore writing of an identifier in the identifier storage device 12 is enabled. By contrast, in the state where the signal processing device 11 is not attached to the identifier storage device 12, even when an identifier is tried to be written in the memory 27, the identifier cannot be written in the memory 27 because the default writing limitation is set.

A second mode has a configuration where the writing limitation is electrically switched depending on attachment/detachment of a control pin for enabling/disabling writing in an IC (Integrated Circuit) constituting the memory 27, to/from the signal processing device 11. In an IC in which writing is enabled in a state where the control pin is in the LOW state, in a state where the signal processing device 11 is not attached, the control pin is electrically pulled-up to the HIGH state. In a state where the signal processing device 11 is attached, the control pin is connected to the GND to be in the LOW state. According to the configuration, only when the signal processing device 11 is attached, the control pin is set to the LOW state, writing is enabled, and an identifier can be written in the memory 27.

As a third mode, a configuration is employed where the supply of the electric power which is to be supplied to the memory 27 is performed only in the case where the signal processing device 11 is attached. According to the configuration, in a state where the signal processing device 11 is not attached to the identifier storage device 12, the electric power is not supplied to the memory 27, and therefore an identifier cannot be written.

Figure 6:
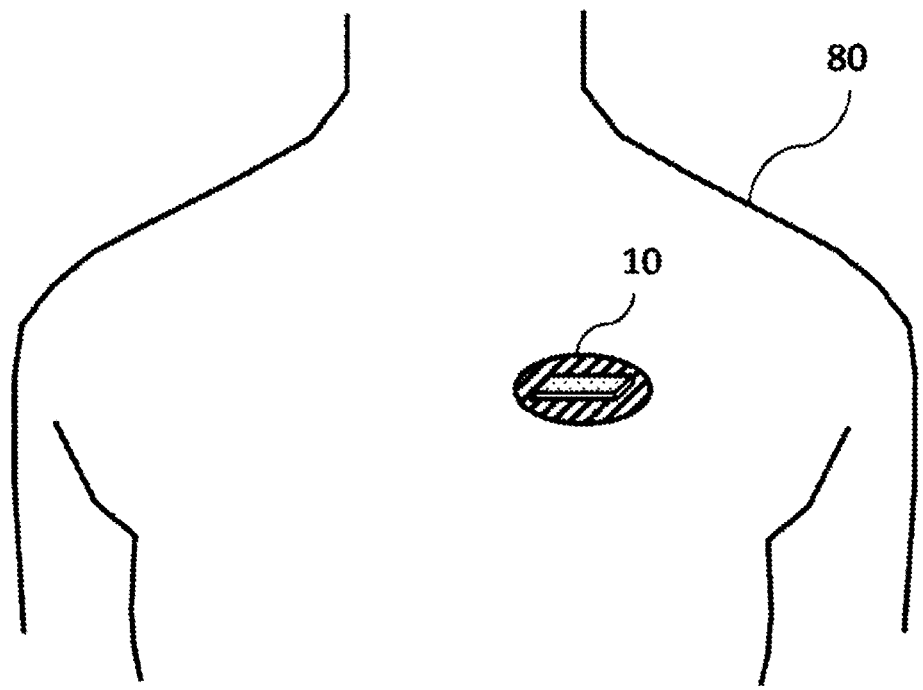
FIG. 6 is a diagram illustrating adherence in which the vital signs sensor of the invention is adhered to the subject through an adhering portion.

A system for attaching the vital signs sensor 10 to the body of the subject 80 will be described. FIG. 6 illustrates a state where the vital signs sensor 10 is attached to the body of the subject 80 to perform measurement. The vital signs sensor 10 includes an adhesive portion, and therefore adheres to the body of the subject 80. In other words, an adhesive material such as that used in an adhesive plaster or the like may be used in the adhesive portion. The adhesive portion may be disposed on either of the signal processing device 11 and the identifier storage device 12. According to the configuration, the vital signs sensor 10 can be attached more easily to the body of the subject 80, and measure a vital sign of the subject 80.

Figure 7:
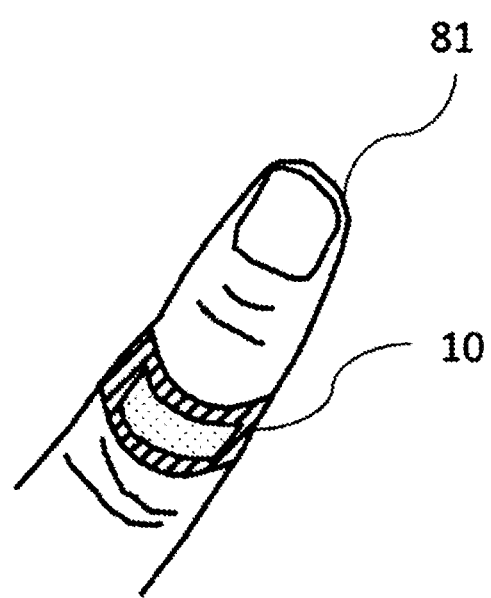
FIG. 7 is a diagram illustrating attachment in which the vital signs sensor of the invention is attached to the finger of the subject.

FIG. 7 illustrates a state where the vital signs sensor 10 is attached to the finger 81 of the subject 80. The vital signs sensor 10 has a shape which allows the sensor to be wound around the finger 81, and therefore can be adequately attached to the finger 81. According to the configuration, the vital signs sensor 10 can be easily attached to the finger 81 in conformity with the shape of the finger. The vital signs sensor 10 may have a shape which conforms to, for example, the shape of either of the arm, the leg, the forehead, and the belly in addition to the finger 81. Depending on a position where the vital signs sensor is to be attached, another shape such as that which is to be used for nipping, or that which is annular may be employed. Namely, the vital signs sensor 10 may have a shape conforming to the portion to which the sensor is to be attached.

Figure 8:
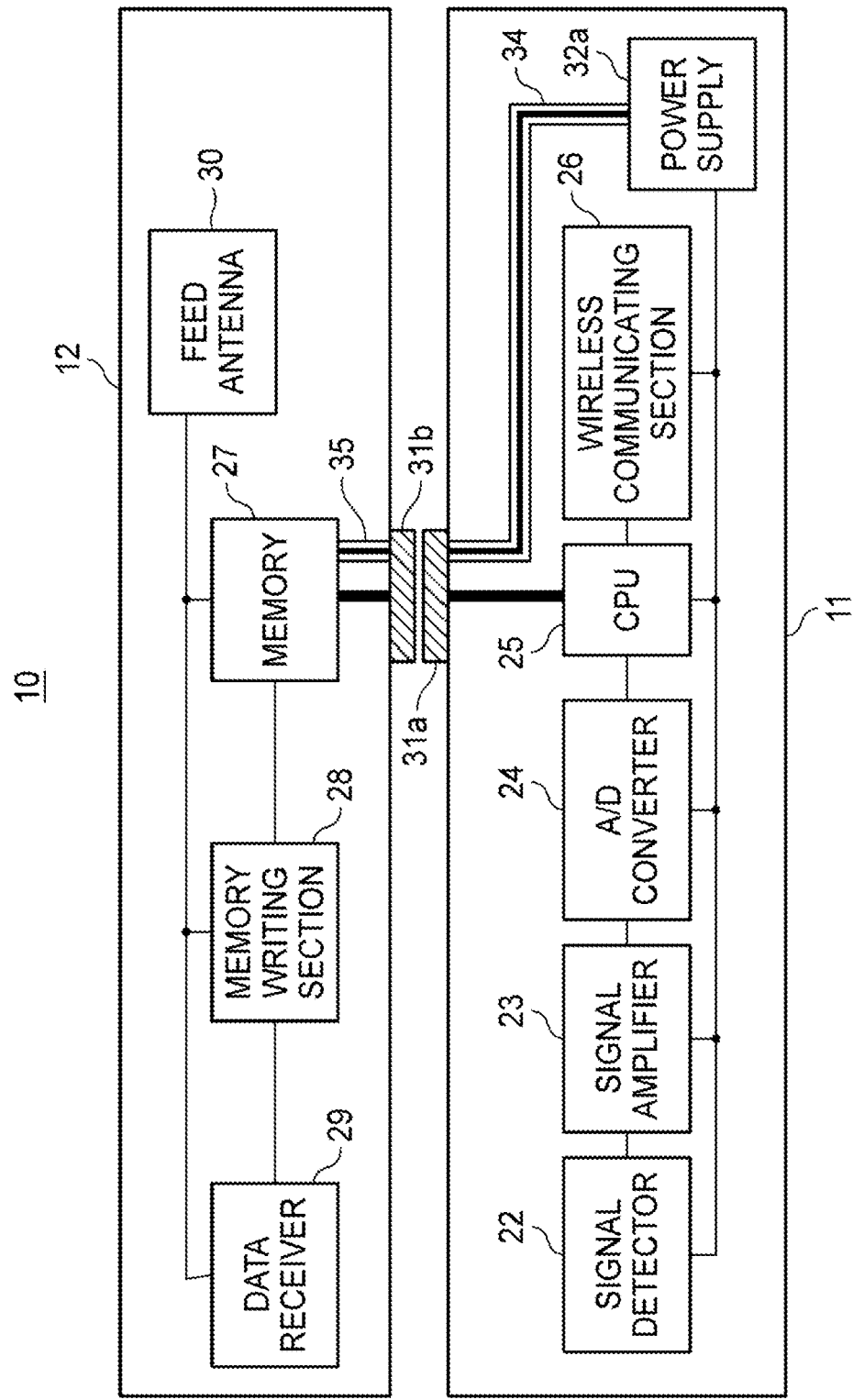
FIG. 8 is a configuration diagram illustrating a power supplying function of the vital signs sensor of the invention.

Hereinafter, modifications of the power supply configuration for the signal processing device 11 and the identifier storage device 12 will be described. FIG. 8 diagrammatically illustrates a functional configuration where the identifier storage device 12 includes a power receiving mechanism 35 to receive power supply from the signal processing device 11. The signal processing device 11 may include a power transmitting mechanism 34 for supplying electric power. In FIG. 8, the power receiving mechanism 35 and the power transmitting mechanism 34 are indicated by triple lines, respectively. The power receiving mechanism 35 and the power transmitting mechanism 34 are wired so as to perform stable supply/reception of electric power, and, for example, configured with electrical considerations for ensuring of the power supply capacity, a countermeasure against noise, and the like. According to the configuration, a power supply is not necessary in the identifier storage device 12, and therefore the identifier storage device 12 can be miniaturized, thinned, and reduced in cost. Alternatively, the power receiving mechanism 35 may be configured so as to receive electric power from an external device other than the signal processing device 11. For example, the identifier storage device 12 may include the power receiving mechanism 35 which receives electric power from a small cell such as a coin cell. In the case where a small cell is employed, even when the power supply is exhausted, the cell can be easily replaced with a new small cell, and therefore continuous use can be realized without suffering from usage time limitation due to the power supply.

Figure 9:
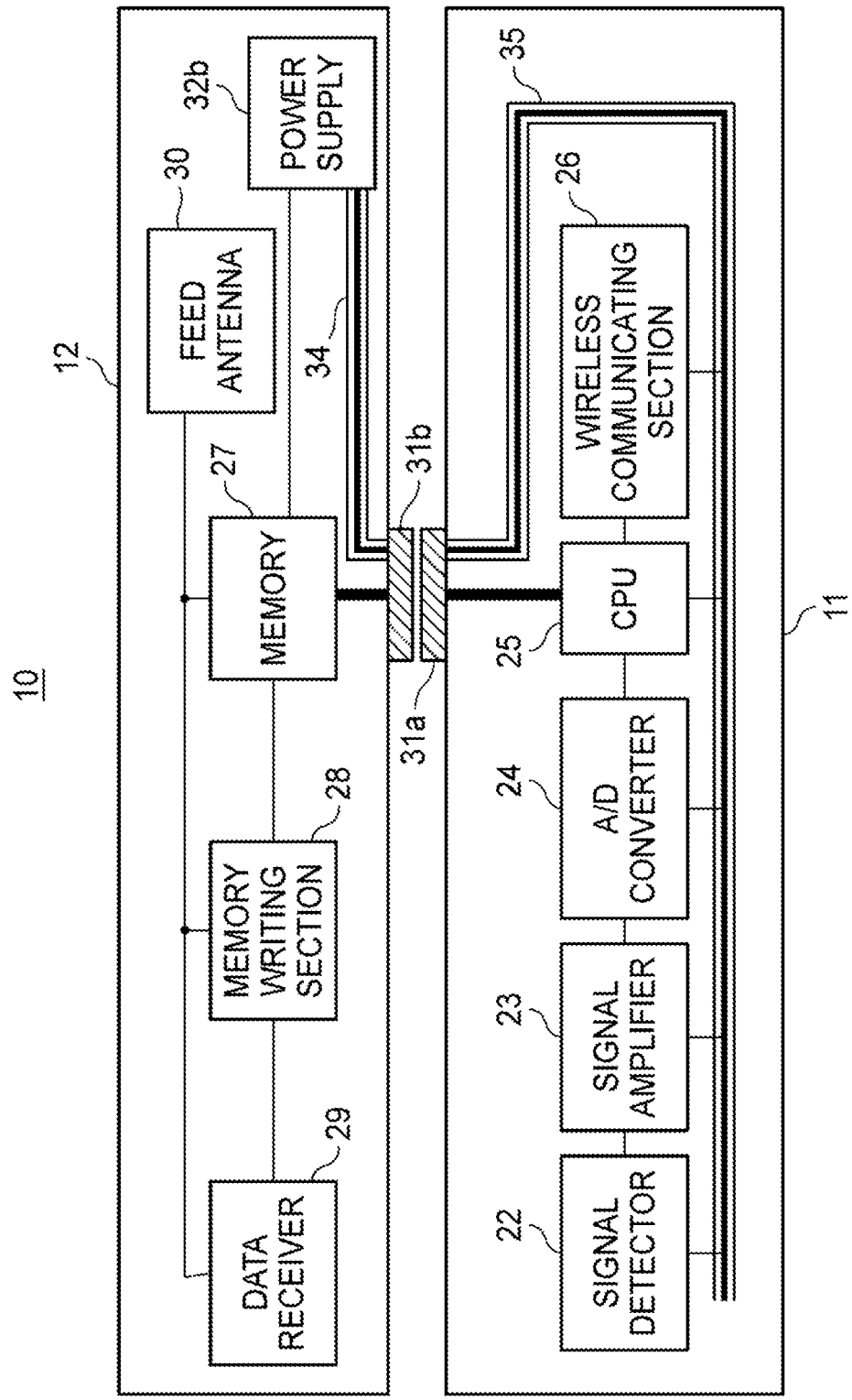
FIG. 9 is a configuration diagram illustrating another power supplying function of the vital signs sensor of the invention.

FIG. 9 diagrammatically illustrates a functional configuration where the signal processing device 11 includes the power receiving mechanism 35 to receive power supply from the identifier storage device 12. The identifier storage device 12 may include the power transmitting mechanism 34 for supplying electric power. In FIG. 9, the power receiving mechanism 35 and the power transmitting mechanism 34 are indicated by triple lines, respectively. According to the configuration, the signal processing device 11 can be configured without including a power supply, and therefore can be miniaturized, thinned, and reduced in cost. Alternatively, the power receiving mechanism 35 may be configured so as to receive electric power from an external device other than the identifier storage device 12. For example, the signal processing device may include the power receiving mechanism 35 which receives electric power from a small cell such as a coin cell. In the case where a small cell is employed, even when the power supply is exhausted, the cell can be easily replaced with a new small cell, and therefore continuous use can be realized without suffering from usage time limitation due to the power supply.

Figure 10:
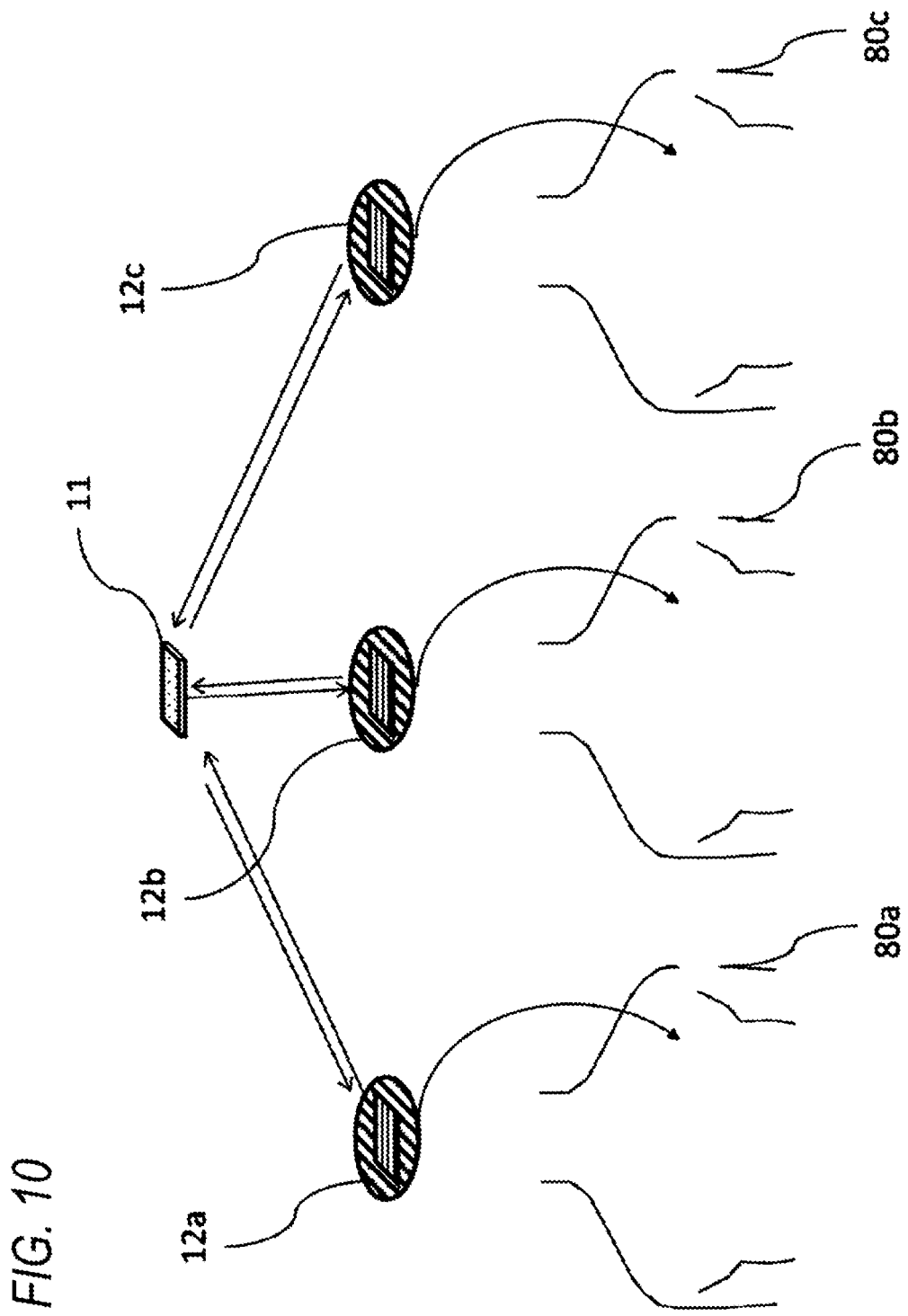
FIG. 10 is a diagram illustrating a manner where the vital signs sensor of the invention is used while replacing identifier storage devices with another one.

Next, a mode where the vital signs sensor is used while a plurality of signal processing devices 11 or identifier storage devices 12 are replaced with one another will be described. FIG. 10 illustrates a use manner where the signal processing device 11 is attached/detached while a plurality of identifier storage devices 12 are replaced with one another. For example, the signal processing device 11 and an identifier storage device 12a for a subject 80a are used in combination, the identifier storage device 12a is then detached from the signal processing device, an identifier storage device 12b for a subject 80b is attached to the signal processing device, and the resulting sensor is used. Also after this use, the identifier storage device 12b can be detached from the signal processing device, an identifier storage device 12c, for a subject 80c can be attached to the signal processing device, and the resulting sensor can be used. Replacement of the identifier storage device 12 can be repeatedly performed. According to the example, the subject 80 which is to be measured can be easily changed while using the single signal processing device 11.

The identifier storage device 12 may be configured as a disposable article. According to the configuration, an identifier which has been used is disposed, and therefore identifiers can be easily managed.

Hereinafter, configuration modes in which the identifier storage device 12 can be configured as a disposable article will be described. In a first mode, an adhesive portion for causing the identifier storage device 12 to adhere to the body of the subject 80 is disposed on the identifier storage device, and the adhesive portion is formed by an adhesive material which exerts one-time adhesion. According to the configuration, it is possible to prevent the identifier storage device from being reused after once peeled off.

In a second mode, the allowable number of writing of an identifier in the memory 27 is set to only one. According to the configuration, after the identifier storage device 12 is once used for a certain subject, it is possible to prevent the identifier storage device from 12 being reused for another subject.

In a third mode, the identifier storage device 12 includes the power supply 32b, and the power supply 32b is configured by a primary cell having a capacity which will be consumed up in one measurement. According to the configuration, it is possible to prevent the identifier storage device from being reused in the next measurement.

Figure 11:
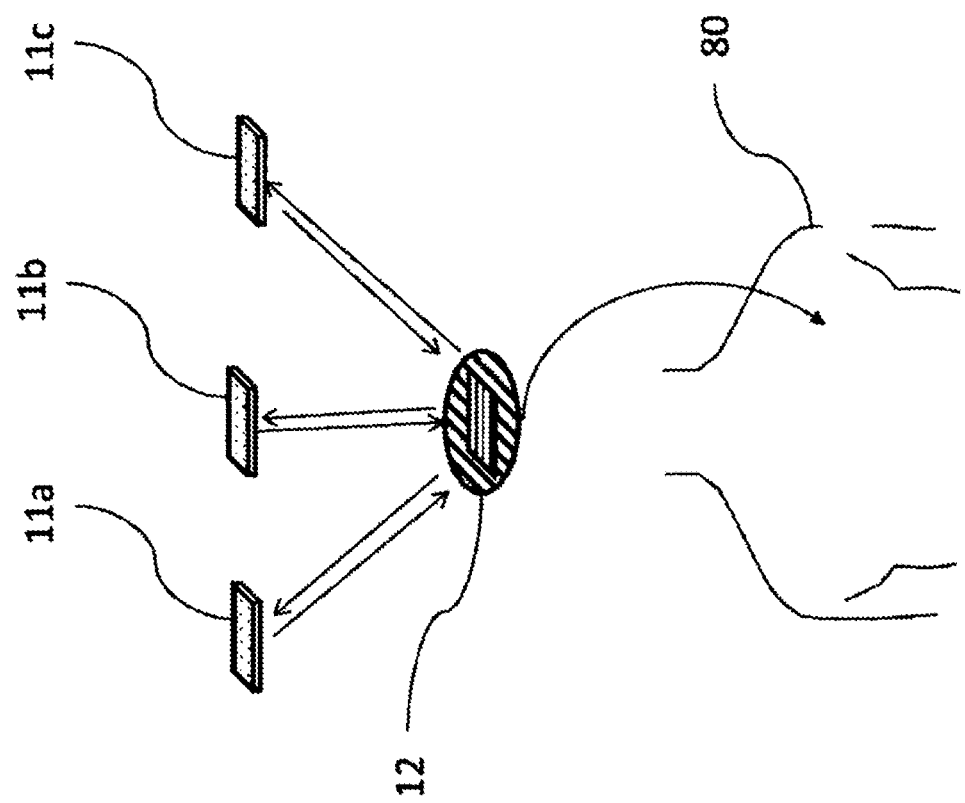
FIG. 11 is a diagram illustrating a manner where the vital signs sensor of the invention is used while replacing signal processing devices with another one.

FIG. 11 illustrates a use manner where the identifier storage device 12 is attached/detached while a plurality of signal processing devices 11 are replaced with one another. For example, the identifier storage device 12 and a signal processing device 11a including a power supply are used in combination, the signal processing device 11a is then detached from the identifier storage device, a signal processing device 11b including a power supply is attached to the identifier storage device, and the resulting sensor is used. Also after this use, the signal processing device 11b can be detached from the identifier storage device, a signal processing device 11c including a power supply can be attached to the identifier storage device, and the resulting sensor can be used. Replacement of the signal processing device 11 can be repeatedly performed. According to the example, the measurement can be easily continued without suffering from limitation of the measurement time due to consumption of the power supply.

An outline of the configuration and effects of the signal processing device 11 and the identifier storage device 12 will be again described. The signal processing device 11 includes the vital sign acquiring section 20 and the signal processing section 21, and has the structure where the signal processing device is attached to and detached from the identifier storage device 12. The vital sign acquiring section 20 detects a vital sign of the subject 80, and outputs the vital sign to the signal processing section 21. The signal processing section 21 reads out the identifier of the subject 80 from the identifier storage device 12 which stores the identifier, correlates the vital sign supplied from the vital sign acquiring section 20 with the identifier, and wirelessly transmits the resulting signal. According to the configuration, the identifier which is to be correlated with the vital sign can be handled as an article, and therefore the identifier can be adequately set or changed.

The identifier storage device 12 includes the memory 27, and has the structure in which the device is attached to and detached from the signal processing device 11. The memory 27 is configured so as to store the identifier of the subject, and to allow the identifier to be read out by the identifier from the signal processing device 11 which acquires the vital sign of the subject 80. According to the configuration, the identifier which is to be correlated with the vital sign can be handled as an article, and therefore the identifier can be adequately set or changed.

Although the invention conducted by the inventors has been specifically described based on the embodiments, the invention is not limited to the above-described embodiments, and it is a matter of course that various changes can be made without departing from the spirit of the invention.

The present application is based on Japanese Patent Application No. 2015-219878, filed on Nov. 9, 2015, the entire contents of which are incorporated herein by reference.

REFERENCE SIGNS LIST 10 vital signs sensor
11 signal processing device
11a, 11b, 11c signal processing device
12 identifier storage device
12a, 12b, 12c identifier storage device
20 vital sign acquiring section
21 signal processing section
22 signal detector
23 signal amplifier
24 A/D converter 25 central processing unit (CPU)
26 wireless communicating section
27 memory
28 memory writing section
29 data receiver
30 feed antenna
31a, 31b attaching/detaching portion
32a, 32b power supply
33 external device
34 power transmitting mechanism
35 power receiving mechanism
80 subject
80a, 80b, 80c subject
81 finger

What is claimed is:

1. A vital signs sensor comprising:
an identifier storage device comprising internal memory that stores an identifier of a subject; and
a signal processing device configured to acquire a vital sign from the subject, to correlate the vital sign with the identifier, and to wirelessly transmit the correlated vital sign and the identifier that is stored in the identifier storage device, wherein:
the identifier storage device has a structure that is attachable to and detachable from the signal processing device,
when the identifier storage device is attached to the signal processing device, the identifier storage device is configured to allow an external device to write the identifier in the internal memory, and
when the identifier storage device is not attached to the signal processing device, the identifier storage device is configured to inhibit the external device from writing the identifier in the internal memory.

2. The vital signs sensor according to claim 1, wherein the identifier storage device or the signal processing device has a portion configured to adhere to a body of the subject.

3. The vital signs sensor according to claim 1, wherein the identifier storage device or the signal processing device is configured to be attached to one of an arm, leg, forehead, finger, and belly of the subject.

4. The vital signs sensor according to claim 1, wherein the identifier storage device further comprises:
a data receiver configured to receive external data; and
a memory writing section configured to write the received data as the identifier in the internal memory.

5. The vital signs sensor according to claim 1, wherein the identifier storage device further comprises a power receiving mechanism configured to receive a power supply from external to the identifier storage device or from the signal processing device.

6. The vital signs sensor according to claim 1, wherein the signal processing device comprises a power receiving mechanism configured to receive a power supply from external to the signal processing device or from the identifier storage device.

7. The vital signs sensor according to claim 1, wherein the signal processing device comprises a detecting mechanism configured to:
detect a connection to the identifier storage device; and
only when the signal processing device is connected to the identifier storage device, enable the identifier to be written in the identifier storage device.

8. The vital signs sensor according to claim 1, wherein:
the identifier storage device is configured to cancel a writing limitation on the internal memory when a connection to the signal processing device is detected, and
the identifier storage device is configured to set the writing limitation on the internal memory when the connection to the signal processing device is not detected.

9. The vital signs sensor according to claim 1, wherein:
the identifier storage device further comprises a control pin configured to enable and disable writing in the internal memory,
when the signal processing device is connected to the identifier storage device, the identifier storage device is configured to cause the control pin to enable the writing, and
when the signal processing device is not connected to the identifier storage device, the identifier storage device is configured to cause the control pin to disable the writing.

10. The vital signs sensor according to claim 1, wherein the identifier storage device is configured to supply electric power to the internal memory only when a connection to the signal processing device is detected.

11. The vital signs sensor according to claim 1, wherein when the identifier, which is read out from the identifier storage device, does not have a predetermined format, the signal processing device is configured to wirelessly transmit an identifier invalidity status instead of the identifier.

12. An identifier storage device comprising:
a memory configured to store an identifier of a subject; and
a structure configured to be attachable to and detachable from a signal processing device, the signal processing device being configured to acquire a vital sign of the subject, wherein:
the identifier storage device is configured to allow the signal processing device to read out the identifier from the memory,
when the identifier storage device is attached to the signal processing device, the identifier storage device is configured to allow an external device to write the identifier in the memory, and
when the identifier storage device is not attached to the signal processing device, the identifier storage device is configured to inhibit the external device from writing the identifier in the memory.

* * * * *